(12) United States Patent
Pai et al.

(10) Patent No.: US 12,421,346 B2
(45) Date of Patent: Sep. 23, 2025

(54) POLYTHIOL COMPOSITION, OPTICAL COMPOSITION, AND OPTICAL PRODUCT

(71) Applicant: SK pucore co., ltd., Ulsan (KR)

(72) Inventors: Jae Young Pai, Gyeonggi-do (KR); Jeong Moo Kim, Gyeonggi-do (KR); Hyuk Hee Han, Gyeonggi-do (KR); Jung Hwan Myung, Gyeonggi-do (KR); Kyeong Hwan You, Gyeonggi-do (KR); Joo Young Jung, Gyeonggi-do (KR); Myung Ok Kyun, Gyeonggi-do (KR); Ji Yeon Ryu, Gyeonggi-do (KR)

(73) Assignee: SK pucore co., ltd., Ulsan (KR)

( * ) Notice: Subject to any disclaimer, the term of this patent is extended or adjusted under 35 U.S.C. 154(b) by 364 days.

(21) Appl. No.: 18/254,170

(22) PCT Filed: Nov. 25, 2021

(86) PCT No.: PCT/KR2021/017483
§ 371 (c)(1),
(2) Date: May 24, 2023

(87) PCT Pub. No.: WO2022/114805
PCT Pub. Date: Jun. 2, 2022

(65) Prior Publication Data
US 2024/0034829 A1 Feb. 1, 2024

(30) Foreign Application Priority Data

Nov. 27, 2020 (KR) .................. 10-2020-0161938
Nov. 24, 2021 (KR) .................. 10-2021-0163011

(51) Int. Cl.
| | | |
|---|---|---|
| *C08G 18/38* | (2006.01) | |
| *C07C 321/14* | (2006.01) | |
| *C08G 18/76* | (2006.01) | |
| *G02B 1/04* | (2006.01) | |

(52) U.S. Cl.
CPC ........ *C08G 18/3876* (2013.01); *C07C 321/14* (2013.01); *C08G 18/387* (2013.01); *C08G 18/7642* (2013.01); *G02B 1/041* (2013.01)

(58) Field of Classification Search
CPC .................. C08G 18/387; C08G 18/3876
See application file for complete search history.

(56) References Cited

U.S. PATENT DOCUMENTS

| | | | | |
|---|---|---|---|---|
| 2013/0303721 A1* | 11/2013 | Jang | ........... | C08G 18/52 |
| | | | | 528/59 |
| 2015/0226879 A1* | 8/2015 | Jang | ........... | G02C 7/02 |
| | | | | 528/85 |
| 2016/0017085 A1* | 1/2016 | Kawaguchi | ........ | C08G 18/7642 |
| | | | | 528/77 |
| 2019/0225755 A1* | 7/2019 | Shim | ........... | C08K 5/37 |

FOREIGN PATENT DOCUMENTS

| | | | | |
|---|---|---|---|---|
| CN | 104402784 A | 3/2015 | | |
| CN | 107311899 A | 11/2017 | | |
| EP | 803744 A2 * | 9/1994 | ............... | G02B 1/04 |
| KR | 10-2001-0100851 A | 11/2001 | | |
| KR | 20120063026 A * | 6/2012 | ............ | C08G 18/06 |
| KR | 10-2013-0050263 A | 5/2013 | | |
| KR | 10-1338568 B1 | 12/2013 | | |
| KR | 10-2014-0029298 A | 3/2014 | | |
| KR | 10-2017-0078139 A | 7/2017 | | |
| KR | 10-2018-0024513 A | 3/2018 | | |
| KR | 10-2019-0060420 A | 6/2019 | | |
| KR | 10-2122703 B1 | 6/2020 | | |
| WO | WO-2014027428 A1 * | 2/2014 | ............ | G02B 1/041 |

OTHER PUBLICATIONS

International Search Report for the International Application No. PCT/KR2021/017483 issued by the International Searching Authority on Mar. 4, 2022.
Notice of Allowance for Korean Patent Application No. 10-2021-0163011 issued by the Korean Patent Office on Sep. 3, 2024.

* cited by examiner

*Primary Examiner* — Michael L Leonard
(74) *Attorney, Agent, or Firm* — IP & T GROUP LLP

(57) ABSTRACT

A polythiol composition according to exemplary embodiments includes a first polythiol compound which provides a maximum peak in a high performance liquid chromatography (HPLC) analysis graph obtained at a wavelength of 230 nm, and a second polythiol compound having a molecular weight greater than that of the first polythiol compound and represented by $C_9H_{20}S_6$. A ratio of a peak area of the second polythiol compound to a peak area of the first polythiol compound, which are measured through the HPLC analysis graph at the wavelength of 230 nm, is 0.05 to 5.0%.

10 Claims, No Drawings

POLYTHIOL COMPOSITION, OPTICAL COMPOSITION, AND OPTICAL PRODUCT

This application is a national stage application of PCT/KR2021/017483 filed on Nov. 25, 2021, which claims priority to Korean Patent Application No. 10-2020-0161938 filed on Nov. 27, 2020, and Korean Patent Application No. 10-2021-0163011 filed on Nov. 24, 2021. The disclosure of each of the foregoing applications is incorporated herein by reference in its entirety.

BACKGROUND

1. Field

The present invention relates to a polythiol composition, an optical composition and an optical product. More particularly, the present invention relates to a polythiol composition including a plurality of thiol-based compounds, an optical composition including the polythiol compound, and an optical product formed from the optical composition.

2. Description of the Related Art

A polythiol compound is widely used, for example, as a raw material for manufacturing a polyurethane resin. For example, a polythiol compound is used to manufacture an optical lens using a polyurethane resin, and quality such as purity of the polythiol compound as a raw material may directly affect the quality of the optical lens.

For example, a polythiourethane-based compound prepared by reacting a polythiol compound and an isocyanate compound may be used as a base material of the optical lens.

For example, Korean Patent Laid-Open Publication No. 10-1338568 discloses a method for synthesizing a polythiol compound by reacting a polyol compound with thiourea to prepare an isothiouronium salt, and then hydrolyzing it using aqueous ammonia.

Depending on the reactivity of the synthesized polythiol compound with the isocyanate compound, transparency of the lens may be reduced or optical non-uniformity may be caused. In addition, depending on the physical properties such as a molecular weight and the number of functional groups of the polythiol compound, mechanical and optical properties of the lens may be changed.

SUMMARY

An object according to exemplary embodiments is to provide a polythiol composition with improved reaction properties and optical properties, and a method for preparation thereof.

An object according to exemplary embodiments is to provide an optical composition including a polythiol composition with improved reaction properties and optical properties.

An object according to exemplary embodiments is to provide an optical product manufactured using the optical composition described above.

According to an aspect of the present invention, there is provided a polythiol composition including: a first polythiol compound which provides a maximum peak in a high performance liquid chromatography (HPLC) analysis graph obtained at a wavelength of 230 nm; and a second polythiol compound having a molecular weight greater than that of the first polythiol compound and represented by $C_9H_{20}S_6$, wherein a ratio of a peak area of the second polythiol compound to a peak area of the first polythiol compound, which are measured through the HPLC analysis graph at the wavelength of 230 nm, is 0.05 to 5.0%.

In some embodiments, the first polythiol compound may include a trifunctional polythiol compound.

In some embodiments, the second polythiol compound may include a trifunctional polythiol compound having a molecular weight greater than that of the first polythiol compound.

In some embodiments, the first polythiol compound may be represented by Formula 1 below:

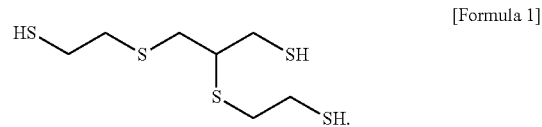 [SMILES: SCCSCC(CS)SCCS]

[Formula 1]

In some embodiments, the second polythiol compound may be represented by Formula 2 below:

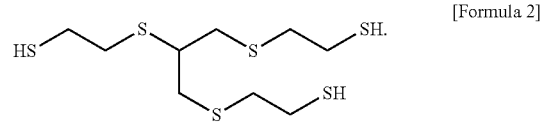 [SMILES: SCCSCC(CSCCS)SCCS]

[Formula 2]

According to another aspect of the present invention, there is provided an optical composition including an isocyanate-based compound and a polythiol composition. The polythiol composition comprises a first polythiol compound which provides a maximum peak in a high performance liquid chromatography (HPLC) analysis graph obtained at a wavelength of 230 nm, and a second polythiol compound having a molecular weight greater than that of the first polythiol compound and represented by $C_9H_{20}S_6$. A ratio of a peak area of the second polythiol compound to a peak area of the first polythiol compound of the polythiol composition, which are measured through the HPLC analysis graph at the wavelength of 230 nm, is 0.05 to 5.0%.

In some embodiments, the first polythiol compound may include a trifunctional polythiol compound, and the second polythiol compound may include a trifunctional polythiol compound having a molecular weight greater than that of the first polythiol compound.

In some embodiments, the first polythiol compound may be represented by Formula 1 below, and the second polythiol compound may be represented by Formula 2:

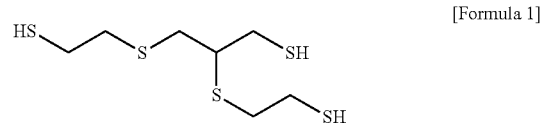 [SMILES: SCCSCC(CS)SCCS]

[Formula 1]

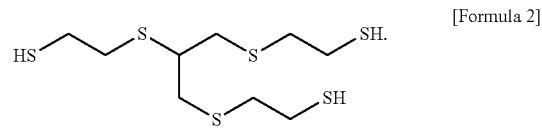 [SMILES: SCCSCC(CSCCS)SCCS]

[Formula 2]

According to another aspect of the present invention, there is provided an optical product including a polythiourethane resin prepared from the polythiol composition or a polymerizable composition.

In some embodiments, the optical product may have a glass transition temperature greater than 86° C.

In some embodiments, the optical product may have a glass transition temperature in a range of 87 to 92° C.

According to the above-described embodiments, the polythiol composition may include, for example, a first polythiol compound including a trifunctional polythiol compound and a second polythiol compound having a molecular weight or carbon number greater than that of the first polythiol compound. The second polythiol compound is included within a predetermined range, so that a reaction rate of the first polythiol compound may be adjusted within an appropriate range, and a glass transition temperature of the composition may be increased.

Accordingly, mechanical durability of an optical lens prepared from the polythiol composition may be improved, and optical defects such as stria or white turbidity may be suppressed.

In some embodiments, by adding 2-mercapoethanol in a reflux process during synthesis of the first polythiol compound, the content of the second polythiol compound may be finely adjusted in a desired range.

DETAILED DESCRIPTION OF THE EMBODIMENTS

Hereinafter, embodiments of the present application will be described in detail. In this regard, the present invention may be altered in various ways and have various embodiments, such that specific embodiments will be illustrated in the drawings and described in detail in the present disclosure. However, the present invention is not limited to the specific embodiments, and it will be understood by those skilled in the art that the present invention is to cover all modifications, equivalents, and alternatives falling within the spirit and scope of the present invention.

Unless otherwise defined, all terms including technical and scientific terms used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to an aspect of the present invention, there is provided a polythiol composition including a plurality of polythiol compounds. The polythiol composition may include a first polythiol compound and a second polythiol compound.

The first polythiol compound may include a polythiol compound serving as a base material in the polythiol composition or an optical composition described below. The first polythiol compound may be included in the polythiol composition as a main polythiol compound thereof.

According to exemplary embodiments, the first polythiol compound may refer to a compound which provides the maximum peak in a high performance liquid chromatography (HPLC) analysis graph for the polythiol composition.

The first polythiol compound may include a trifunctional polythiol compound. As a non-limiting example, the trifunctional polythiol compound may include a compound represented by $C_7H_{16}S_5$. In one embodiment, the trifunctional polythiol compound may include a compound represented by Formula 1 below.

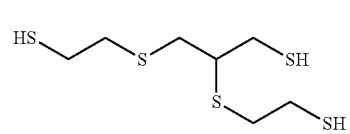

[Formula 1]

As described above, the trifunctional polythiol compound may be used or included as the first polythiol compound. the trifunctional polythiol compound has relatively higher economic efficiency and lower viscosity than the tetrafunctional polythiol compound, thereby improving processability and the like.

The polythiol composition according to exemplary embodiments may further include a second polythiol compound. For example, the second polythiol compound may be included or added as a reactivity regulator or reaction rate regulator of the polythiol composition.

In one embodiment, the second polythiol compound may include a polythiol compound having a molecular weight or carbon number greater than that of the first polythiol compound. In one embodiment, the second polythiol compound may have the same number of functional groups as the first polythiol compound. In this case, the first polythiol compound and the second polythiol compound may include a trifunctional polythiol compound, respectively.

In some embodiments, the second polythiol compound may include a compound represented by $C_9H_{20}S_6$. In some embodiments, the second polythiol compound may include a trifunctional thiol compound represented by Formula 2 below.

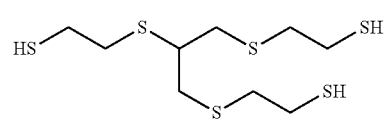

[Formula 2]

As described above, the second polythiol compound may be included in the composition together with the first polythiol compound to function as a regulator or buffer for low glass transition temperature and high reaction rate of the first polythiol compound.

Accordingly, it is possible to suppress the generation of stria due to excessive reaction rate and flowability of the trifunctional polythiol compound. In addition, the overall thiol value and liquid refractive index of the polythiol composition may be finely adjusted through the second polythiol compound.

Further, mechanical properties such as casting stability of the lens may also be improved through the action of increasing the glass transition temperature of the polythiol composition.

Therefore, an optical product such as a lens having uniform optical properties with inhibited coloring and stria phenomena may be obtained by using the polythiol composition. In addition, chemical stability of the polythiol composition or the optical product may be improved, and thereby the white turbidity phenomenon of the lens may be effectively suppressed.

According to exemplary embodiments, a ratio of a peak area (%) of the second polythiol compound to a peak area (%) of the first polythiol compound, which are measured through a high performance liquid chromatography (HPLC) analysis graph obtained at a wavelength of 230 nm, may be in a range of 0.05 to 5.0%.

For example, a ratio of polythiol compounds in the polythiol composition, which is represented by Equation 1 below, may be in the range of 0.05 to 5.0%.

{(HPLC peak area of the second polythiol compound)/(HPLC peak area of the first polythiol compound)}×100(%)  [Equation 1]

For example, if the ratio of the second polythiol compound is excessively increased, the reactivity between the polythiol composition and the isocyanate-based compound may be excessively reduced. Accordingly, elution of an adhesive component of a tape included in a mold and white turbidity phenomena may be caused during a lens manufacturing process.

For example, when the ratio of the second polythiol compound is excessively decreased, sufficient effects of increasing the glass transition temperature and adjusting the reactivity through the second polythiol compound may not be implemented.

Accordingly, as the peak area ratio defined by Equation 1 is maintained in the range of 0.05 to 5.0%, the reaction rate may be appropriately maintained, thereby effectively suppressing stria/white turbidity and improving durability of optical products.

Preferably, the ratio of the polythiol compounds may be 0.05 to 4.9% or 0.08 to 4.85%. More preferably, the ratio of the polythiol compounds may be 0.5 to 4.9%, 1.0 to 4.9%, 1.0 to 3.0%, or 1.0 to 2.0%.

According to another aspect of the present invention, there is provided a method for preparing a polythiol composition including a plurality of polythiol compounds. As described above, the polythiol composition may include at least two different trifunctional polythiol compounds, and may include the first polythiol compound and the second polythiol compound.

The method for preparing a polythiol composition according to exemplary embodiments may include the following steps, processes or actions.

The method for preparing a polythiol composition according to exemplary embodiments may include at least one of the steps, processes or actions described as S10, S20, S30 and S40 below. It should be understood that the following terms "S10, S20, S30 and S40" are used to distinguish processes for the convenience of description and are not intended to limit the sequential order thereof. For example, some or all of the processes of S10, S20, S30 and S40 below may be sequentially conducted, and/or may be conducted with altered order according to process conditions.

S10) Reacting 2-mercaptoethanol and epihalohydrin to produce a polyol intermediate S20) Additionally adding 2-mercaptoethanol while reacting the polyol intermediate with thiourea under acidic conditions to produce an isothiouronium salt S30) Converting the isothiouronium salt into a polythiol compound.

For example, the polyol intermediate may be produced by reacting 2-mercaptoethanol and epihalohydrin in step S10.

For example, a process of synthesizing the polyol intermediate may be represented by Scheme 1 below.

[Scheme 1]

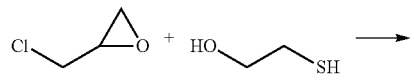

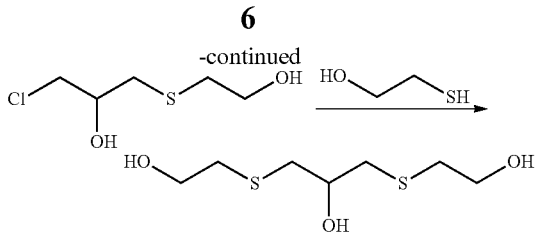

As shown in Scheme 1, 2-mercaptoethanol and epihalohydrin may be reacted to produce a preliminary polyol intermediate such as a diol intermediate. The preliminary polyol intermediate may be additionally reacted with 2-mercaptoethanol to produce a polyol intermediate such as a triol intermediate.

In one embodiment, in the reaction step of epihalohydrin and 2-mercaptoethanol for synthesizing a trifunctional polythiol compound, a metal-containing catalyst such as sodium hydroxide or potassium hydroxide may be used.

As illustrated in Scheme 1 above, epichlorohydrin may be used as the epihalohydrin. For example, a content of 2-mercaptoethanol may be 0.5 to 3 moles, preferably 0.7 to 2 moles, and more preferably 0.9 to 1.1 moles based on 1 mole of epihalohydrin. The metal-containing catalyst may be used in an amount of 0.001 to 0.1 moles based on 1 mole of epihalohydrin.

The production of the preliminary polyol intermediate and the polyol intermediate may be carried out under cooling conditions, and may be performed, for example, at a reaction temperature in a range of −5 to 40° C., preferably 0 to 30° C., and more preferably carried out 5 to 20° C.

For example, in step S20, 2-mercaptoethanol may be additionally added while reacting the polyol intermediate with thiourea under acidic conditions to produce an isothiouronium salt.

A reflux process under acidic conditions may be used in the production of isothiouronium salts. In order to form such acidic conditions, acidic compounds such as hydrochloric acid, hydrobromic acid, iodic acid, sulfuric acid, phosphoric acid, and the like may be used. The reflux temperature may be 90 to 120° C., preferably 100 to 120° C., and may be performed for about 1 to 10 hours.

In the step of producing an isothiouronium salt, 2-mercaptoethanol may be additionally added to induce an addition reaction with the polyol intermediate. Accordingly, for example, the synthesis of the second polythiol compound represented by Formula 2 and having a relatively high molecular weight or the number of carbons may be induced.

The amount of 2-mercaptoethanol additionally added may be 0.05 to 5.0% by weight ("wt. %") based on the weight of thiourea. Within the above addition amount range, the above-described ratio of the polythiol compounds represented by Equation 1 may be easily obtained. In one embodiment, the amount of 2-mercaptoethanol additionally added is 0.5 to 5 wt. %, preferably 1 to 5 wt. %, and more preferably 1 to 3 wt. %, or 1 to 2 wt. % based on the weight of thiourea.

For example, in step S30, the produced isothiouronium salt may be converted into a polythiol compound.

According to exemplary embodiments, the isothiouronium salt may be hydrolyzed under basic conditions to produce a polythiol compound.

For example, a basic aqueous solution may be added to a reactive solution containing the isothiouronium salt to conduct hydrolysis. The basic aqueous solution may include alkali-metal hydroxide and/or alkaline earth metal hydroxide, such as NaOH, KOH, LiGH, Ca(OH)$_2$, etc.

In one embodiment, the reaction solution containing the isothiouronium salt is cooled to a temperature of 20 to 60° C., preferably 25 to 55° C., and more preferably 25 to 50° C. Thereafter, the basic aqueous solution may be added.

In one embodiment, an organic solvent may be added before adding the basic aqueous solution. An organic solvent having low reactivity or substantially no reactivity and a boiling point exceeding a thiolation reaction temperature may be used so that a thiolation reaction proceeds stably.

Examples of the organic solvent may include toluene, xylene, chlorobenzene, dichlorobenzene and the like. Preferably, toluene may be used in consideration of reaction stability and toxicity from the organic solvent.

For example, the above-described steps S20 and S30 may be represented together by Scheme 2 below.

In some embodiments, a residual moisture content of the polythiol compound or polythiol composition may be 1,000 ppm or less, preferably in a range of 100 to 500 ppm, and more preferably 150 to 400 ppm.

In some embodiments, a liquid refractive index of the polythiol composition at 25° C. may be 1.629 to 1.635, preferably 1.629 to 1.631, and more preferably 1.6295 to 1.6305.

In some embodiments, a thiol value (SHV) of the polythiol composition may be about 88.0 to 90.0 g/eq. Preferably, the SHV is 88.0 to 89.5 g/eq.

The SHV may be measured by dividing the sample weight by the consumed iodine equivalent when titrating a polythiol composition sample using a 0.1N iodine standard solution.

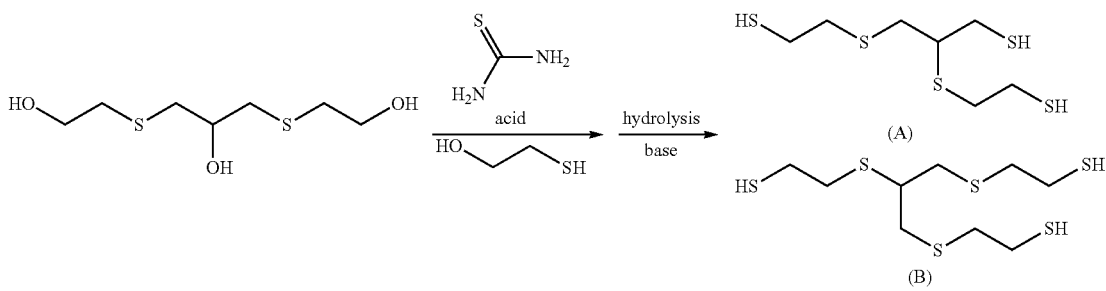

[Scheme 2]

As described above, in the thiourea reaction/reflux process for production of the isothiouronium salt, 2-mercaptoethanol may be additionally added in an amount within a predetermined range. Accordingly, as shown in Scheme 2, a polythiol composition including both the first polythiol compound (A) which is target polythiol compound and the second polythiol compound (B) may be obtained.

The polythiol compound or the polythiol composition obtained as described above may be further purified. For example, by repeatedly performing acid washing and water washing processes, impurities included in the polythiol compound may be removed, in addition, the transparency of the optical material prepared from the polythiol composition may be improved. Thereafter, drying, filtration, etc. may be additionally performed.

In one embodiment, an aqueous layer may be separated or removed through layer separation after proceeding with the hydrolysis. Acid washing may be carried out at a temperature of about 20 to 50° C., and preferably about 30 to 40° C. for 20 minutes to 1 hour, or 20 to 40 minutes by introducing an acid solution to the obtained organic phase solution.

After the acid washing, the water washing process may be conducted by adding degassed water having a dissolved oxygen concentration adjusted to 5 ppm or less, preferably 3 ppm or less, and more preferably 2 ppm or less. The water washing process may be conducted at a temperature of about 20 to 50° C., preferably about 35 to 45° C. for 20 minutes to 1 hour, or 20 to 40 minutes. The water washing process may be repeated two or more times, for example, may be conducted 3 to 6 times.

After the acid washing and the water washing processes, the residual organic solvent and moisture may be removed by heating under reduced pressure, followed by filtering through a filter to obtain a polythiol compound with high purity.

According to the above-described embodiments, the production of the second polythiol compound may be controlled through the divided introduction of 2-mercaptoethanol. However, the present invention is not limited to the above-described preparation method, and the second polythiol compound may be separately introduced to the polythiol composition in an amount corresponding to the peak area within the above-described range. Additionally, the amount of the second polythiol compound may be adjusted through other process conditions such as a reaction temperature, and reaction time in addition to the 2-mercaptoethanol.

According to another aspect of the present invention, there is provided an optical composition (e.g., a polymerizable composition for an optical material) including the above-described polythiol composition.

The optical composition may include the polythiol composition and an isocyanate-based compound. Alternatively, the polymerizable composition for an optical material may include the first polythiol compound, the second polythiol compound, and the isocyanate-based compound.

The isocyanate-based compound may include a compound that is useable as a monomer for synthesizing polythiourethane. In a preferred embodiment, the isocyanate-based compound may include 1,3-bis(isocyanatomethyl) cyclohexane, hexamethylene diisocyanate, isophorone diisocyanate, xylene diisocyanate, toluene diisocyanate and the like. These may be used alone or in combination of two or more thereof.

The optical composition may further include additives such as a release agent, a reaction catalyst, a thermal stabilizer, an ultraviolet absorber, a bluing agent and the like.

Examples of the release agent may include a fluorine-based nonionic surfactant having a perfluoroalkyl group, a hydroxyalkyl group or a phosphoric acid ester group; a silicone-based nonionic surfactant having a dimethylpolysiloxane group, a hydroxyalkyl group or a phosphoric acid ester group; alkyl quaternary ammonium salts such as trimethylcetyl ammonium salt, trimethylstearyl, dimethylethylcetyl ammonium salt, triethyldodecyl ammonium salt, trioctylmethyl ammonium salt and diethylcyclohexadodecyl ammonium salt; acidic phosphoric acid ester and the like. These may be used alone or in combination of two or more thereof.

As the reaction catalyst, a catalyst used in the polymerization reaction of a polythiourethane resin may be used. For example, dialkyltin halide catalysts, such as dibutyltin dichloride and dimethyltin dichloride; dialkyltin dicarboxylate catalysts such as dimethyltin diacetate, dibutyltin dioctanoate, and dibutyltin dilaurate; dialkyltin dialkoxide catalysts such as dibutyltin dibutoxide and dioctyltin dibutoxide; dialkyltin dithio alkoxide catalysts such as dibutyltin di(thiobutoxide); dialkyltin oxide catalysts such as di(2-ethylhexyl)tin oxide, dioctyltin oxide, and bis(butoxydibutyltin) oxide; dialkyltin sulfide catalysts, and the like may be used. These may be used alone or in combination of two or more thereof.

As examples of the ultraviolet absorber, benzophenone-based, benzotriazole-based, salicylate-based, cyanoacrylate-based, oxanilide-based compounds, and the like may be used. As examples of the thermal stabilizer, metal fatty acid salt-based, phosphorus-based, lead-based, organotin-based compounds, and the like may be used. These may be used alone or in combination of two or more thereof.

The bluing agent may be included as a color regulator of the optical material prepared from the polythiourethane resin. For example, the bluing agent may have an absorption band in a wavelength band from orange to yellow in a visible light region.

Examples of the bluing agent may include a dye, a fluorescent whitening agent, a fluorescent pigment, an inorganic pigment, and the like, and may be appropriately selected according to physical properties or resin color required for the optical product to be manufactured. When the dye is used as the bluing agent, for example, a dye having a maximum absorption wavelength of 520 to 600 nm, and preferably 540 to 580 nm may be used. Preferably, anthraquinone-based dyes may be used.

The polythiourethane resin may be produced through a polymerization reaction of the polythiol compound included in the polythiol composition with the isocyanate-based compound, and the polymerization reaction rate may be adjusted or controlled by the reactivity control action of the second polythiol compound included in the polythiol composition.

Accordingly, yellowing or white turbidity phenomenon may be prevented, the generation of stria may be suppressed, and an optical product in which uniform and improved optical properties are maintained for a long period of time may be obtained.

In some embodiments, the reaction rate of the optical composition included in Equation 1 described below may be maintained in a range of 0.25 to 0.35, preferably in a range of 0.25 to 0.32, and more preferably in a range of 0.25 to 0.30 by the second polythiol compound.

In some embodiments, based on a total weight of the optical composition, the polythiol-based composition or polythiol compound may be included in a content of about 40 to 60 wt. %, and the isocyanate-based compound may be included in a content of about 40 to 60 wt. %, and the additive may be included in a content of about 0.01 to 1 wt. %.

As described above, the second polythiol compound may be included in the polythiol composition, therefore, may be contained in the optical composition along with the polythiol composition. In one embodiment, the second polythiol compound may be added to the composition including the isocyanate-based compound thus to be contained in the optical composition. In one embodiment, the second polythiol compound may be mixed with the first polythiol compound and the isocyanate-based compound thus to be contained in the optical composition.

Further, according to another aspect of the present invention, an optical product manufactured through the above-described polymerizable composition may be provided.

For example, after degassing the polymerizable composition under reduced pressure, the resultant composition may be injected into a mold for molding an optical material. Injection into the mold may be performed, for example, in a temperature range of 20 to 40° C., and preferably 20 to 35° C.

After the injection into the mold, the temperature may be gradually increased, and a polymerization reaction of the polythiourethane resin to proceed. The polymerization temperature may range from 20 to 200° C., and preferably 25 to 125° C.

The polymerization temperature may range from 20 to 150° C., and preferably 25 to 125° C. For example, the maximum polymerization temperature may range from 100 to 150° C., preferably 110 to 140° C., and more preferably 115 to 130° C.

The heating rate may be 1 to 10° C./min, preferably 3 to 8° C./min, and more preferably 4 to 7° C./min. The polymerization time may be 10 to 20 hours, and preferably 15 to 20 hours.

For example, a lens having uniform optical properties and mechanical properties may be easily obtained by appropriately controlling the reaction rate within the above temperature range.

After polymerization, the polymerized polythiourethane resin may be separated from the mold to obtain an optical product. In one embodiment, after separation from the mold, a curing process may be further conducted. The curing process may be conducted in a range of 100 to 150° C., preferably 110 to 140° C., and more preferably 115 to 130° C. for about 1 to 10 hours, preferably 2 to 8 hours, and more preferably 3 to 6 hours.

After polymerization, the polymerized polythiourethane resin may be separated from the mold to obtain an optical product. The optical product may be manufactured in the form of a spectacle lens, a camera lens, a light emitting diode, etc. according to a shape of the mold.

The refractive index of the optical product may be adjusted according to the type and/or content ratio of the polythiol compound and the isocyanate-based compound used in the polymerizable composition for an optical material. For example, the refractive index of the optical product may be adjusted in a range of 1.56 to 1.78, 1.58 to 1.76, 1.60 to 1.78, or 1.60 to 1.76, and preferably in a range of 1.65 to 1.75 or 1.69 to 1.75.

As described above, the glass transition temperature (Tg) and heat resistance of an optical product may be increased by the second polythiol compound included in the polythiol composition.

In some embodiments, the glass transition temperature of the optical product may be 85° C. or more, preferably greater than 86° C., and may be, for example, 85 to 100° C. Preferably, the glass transition temperature of the optical product is 86 to 95° C., and more preferably 86 to 93° C., 87 to 92° C., or 87 to 90° C.

The optical product may be improved by further conducting surface treatment such as anti-fouling, color imparting, hard coat, surface polishing, hardness strengthening and the like.

Hereinafter, embodiments provided in the present application will be further described with reference to specific experimental examples. However, the following experimental examples only illustrate the present invention and are not intended to limit the appended claims, and those skilled in the art will obviously understand that various alterations and modifications are possible within the scope and spirit of the present invention. Such alterations and modifications are duly included in the appended claims.

Example 1

1) Synthesis of Trifunctional Polythiol Compound

Into a reactor, 200 parts by weight ("wt. parts") of 2-mercaptoethanol (2-ME), 200 wt. parts of degassed water (dissolved oxygen concentration of 2 ppm), and 61.4 wt. parts of sodium hydroxide were added. In the reactor, 118.4 wt. parts of epichlorohydrin was slowly added dropwise at 9 to 13° C. and stirred for 3 hours.

Then, 360.5 wt. parts of thiourea and 3.6 wt. parts of 2-mercaptoethanol (1 wt. % based on thiourea) were added, and 666.8 wt. parts of hydrochloric acid having a purity of 36% was input, then stirred for 3 hours while refluxing at 110° C., such that a thiuronium chloride reaction was proceeded.

After cooling the obtained reaction solution to 45° C., 589.7 wt. parts of toluene was added and cooled to 26° C. again, and 829 wt. parts of 33 wt. % sodium hydroxide was added over 25 minutes at 25 to 45° C., followed by conducting hydrolysis at 40 to 60° C. for 3 hours.

Then, after performing layer separation for 1 hour, the aqueous layer was discarded, 234 wt. parts of 36% hydrochloric acid was added to the obtained toluene solution, and acid washing was conducted once at 33 to 40° C. for 30 minutes. After acid washing, 530 wt. parts of degassed water (dissolved oxygen concentration of 2 ppm) was added, and washing was conducted at 35 to 45° C. for 30 minutes. The washing was conducted 4 times. After removing toluene and residual moisture under heating and reduced pressure, it was filtered under reduced pressure through a PTFE type membrane filter thus to obtain 260 wt. parts of polythiol composition including the trifunctional polythiol compound represented by Formula 1 as a main component.

2) Preparation of Polymerizable Composition for an Optical Material and Manufacturing of Lens 48.0 wt. parts of the polythiol composition prepared as described above was uniformly admixed with 52.0 wt. parts of xylene diisocyanate, 0.01 wt. parts of dibutyltin chloride and 0.1 wt. parts of phosphoric acid ester release agent produced by ZELEC® UN tepan. Thereafter, a defoaming process was conducted at 600 Pa for 1 hour to prepare a polymerizable composition for an optical material.

Then, the composition filtered through a 3 m Teflon filter was injected into a mold provided with a glass mold and a tape. A temperature of the mold was slowly increased from 25 to 120° C. at a rate of 5° C./min, and polymerization was performed at 120° C. for 18 hours. After the polymerization was completed, the mold was separated, followed by further curing the product at 120° C. for 4 hours to manufacture a lens sample.

Example 2-5 and Comparative Example

Polythiol compositions and lens samples were prepared in the same manner as in Example 1, except that the amount of 2-mercaptoethanol introduced in the reflux process under acidic conditions was changed as described in Table 1 below.

Experimental Example (1) Evaluation of Thiol Value (SHV)

About 0.1 g of the polythiol composition prepared in each of the examples and comparative examples was introduced into a beaker, and 25 mL of chloroform was added, followed by stirring the mixture for 10 minutes. Then, 10 mL of methyl alcohol MeOH was added and stirred again for 10 minutes, and then, the resultant solution was titrated with a 0.1N iodine standard solution, followed by measuring SHV according to Equation 1 below (theoretical value: 86.8 g/eq).

SHV (g/eq.)=Sample weight (g)/{0.1×Amount of iodine consumed (L)}   [Equation 1]

(2) Liquid Refractive Index

For the polythiol compositions synthesized in the examples and comparative examples, the refractive index at 25° C. was measured using a liquid refractometer (RA-600 (Kyoto Electronics)).

(3) HPLC Analysis

In the polythiol compositions according to the examples and comparative examples, peak areas (%) of the polythiol compound of Formula 1 (Compound A) and the polythiol compound of Formula 2 (Compound B) included in the composition were measured, and the peak area ratio of the polythiol compounds was calculated through HPLC analysis performed under the following conditions.

<HPLC Analysis Condition>
  i) Equipment: LC 30A System (Shimadzu)
  ii) Column: MC-Pack ODS-A 150 mm×6 mm (S-5 μm, 12 nm)
  iii) Mobile phase gradient: Acetonitrile (0.1% Formic Acid)Water (0.01M Ammonium Formate)=40:60-100:0
  vi) Wavelength: 230 nm, Flow rate: 1.0 ml/min, Injection amount: 10 μl, Sample pretreatment: sample:solvent=0.1 g:10 g The retention time of compound A was measured in a range of 15 to 17 minutes, and the retention time of compound B was measured in a range of 17.5 to 19 minutes.

Specific compounds corresponding to the peaks of Compound A and Compound B in the HPLC graph were identified through liquid chromatography-mass spectrometry (LC-MS) (Q Exactive: Thermo Fisher Scientific). Specifically, the molecular weight corresponding to Compound B was measured as 320.62 (actual molecular weight: 319.99), thereby confirming the existence of Compound B.

(4) Evaluation of Stria

As described above, a lens sample having a diameter of 75 mm and −4.00 D was prepared using the polymerizable composition according to each of the examples and comparative examples. A light from a mercury lamp light source was transmitted through the prepared lens sample, and the transmitted light was projected on a white plate to determine the presence or absence of stria according to the presence or absence of contrast. Standards for evaluation are as follows.
  ○: Stria not observed
  Δ: Fine partial stria observed
  x: Stria clearly observed visually (5) Evaluation of White Turbidity of the Lens For the lens samples of the examples and comparative examples prepared as described above, each sample was irradiated from a projector in a dark room, and it was visually confirmed whether the lens had haze or an opaque material.

(6) Measurement of Polymerization Reaction Rate (Reactivity Slope)

Using a non-contact viscometer of EMS-1000 (KEM), the standard viscosity (Standard cps) was first confirmed with a viscosity standard solution (Brookfield, 1000 cps, 25° C.). Thereafter, the viscosity was measured at 10° C. for 24 hours for the polymerizable compositions according to the examples and comparative examples, respectively. Using the measured values, mathematical formulation ("mathematization") was conducted with an X-axis as a time and a Y-axis as a viscosity while converting the Y-axis in a logarithmic scale as shown in Mathematical Equation 1 below, and then the reaction rate was derived therefrom.

$$Y = a \times \exp(b \times X) \quad \text{[Mathematical Equation 1]}$$

In Equation 1, 'a' value represents an initial viscosity (cps) while 'b' value represents the reaction rate, the measured value was expressed by rounding to the two decimal places of the measured value.

(7) Measurement of Glass Transition Temperature (Tg)

The glass transition temperature (Tg) of the lens samples of the examples and comparative examples was measured using a penetration method (load: 50 g, pin tip diameter: Φ0.5 mm, and heating rate: 10° C./min) by using a thermomechanical analyzer (TMA Q400, TA instruments).

Evaluation results are shown together in Tables 1 and 2 below.

Referring to Tables 1 and 2, in the case of the examples in which 2-ME was added in the reflux process and the compound of Formula 2 (Compound B) was included in the above range, it was confirmed that the mechanical durability of the lens could be improved while the glass transition temperature was increased (e.g., greater than 86° C. or 87° C. or more).

In addition, while the reaction rates of the polythiol compositions of the examples were maintained in an appropriate range, stria and white turbidity phenomena of the lens did not substantially occur.

What is claimed is:

1. A polythiol composition comprising:
   a first polythiol compound which provides a maximum peak in a high performance liquid chromatography (HPLC) analysis graph obtained at a wavelength of 230 nm; and
   a second polythiol compound having a molecular weight greater than that of the first polythiol compound and represented by $C_9H_{20}S_6$,
   wherein a ratio of a peak area of the second polythiol compound to a peak area of the first polythiol compound, which are measured through the HPLC analysis graph obtained at the wavelength of 230 nm, is 0.05 to 5.0%.

2. The polythiol composition according to claim 1, wherein the first polythiol compound includes a trifunctional polythiol compound.

TABLE 1

| | Addition amount of 2-ME in reflux process (wt. % based on thiourea) | Physical property of polythiol composition | | | | |
| --- | --- | --- | --- | --- | --- | --- |
| | | HPLC analysis at 230 nm | | | | |
| | | Peak area (Compound B) (%) | Peak area (Compound A) (%) | Ratio defined by Equation 1 (B/A) × 100 (%) | SHV (g/ea) | Liquid refractive index |
| Example 1 | 1 wt. % | 0.92 | 90.12 | 1.02 | 88.4 | 1.6296 |
| Example2 | 2 wt. % | 1.56 | 89.43 | 1.74 | 88.6 | 1.6300 |
| Example3 | 5 wt. % | 4.19 | 86.39 | 4.85 | 89.5 | 1.6302 |
| Example4 | 0.5 wt. % | 0.56 | 91.14 | 0.61 | 88.3 | 1.6294 |
| Example 5 | 0.05 wt. % | 0.07 | 92.69 | 0.08 | 88.1 | 1.6293 |
| Comparative Example 1 | — | 0.02 | 92.72 | 0.02 | 87.7 | 1.6292 |
| Comparative Example2 | 0.03 wt. % | 0.04 | 92.61 | 0.04 | 87.8 | 1.6292 |
| Comparative Example3 | 6 wt. % | 4.53 | 85.02 | 5.33 | 90.1 | 1.6306 |

TABLE 2

| | Physical property of lens | | | |
| --- | --- | --- | --- | --- |
| | Stria | White turbidity | Reaction rate | Tg(° C.) |
| Example 1 | ○ | ○ | 0.30 | 88 |
| Example2 | ○ | ○ | 0.28 | 89 |
| Example3 | ○ | ○ | 0.25 | 92 |
| Example4 | ○ | ○ | 0.31 | 87 |
| Example 5 | ○ | ○ | 0.32 | 87 |
| Comparative Example 1 | Δ | ○ | 0.37 | 84 |
| Comparative Example2 | Δ | ○ | 0.36 | 84 |
| Comparative Example3 | ○ | x | 0.22 | 92 |

3. The polythiol composition according to claim 2, wherein the second polythiol compound includes a trifunctional polythiol compound having a molecular weight greater than that of the first polythiol compound.

4. The polythiol composition according to claim 1, wherein the first polythiol compound is represented by Formula 1 below, and the second polythiol compound is represented by Formula 2 below:

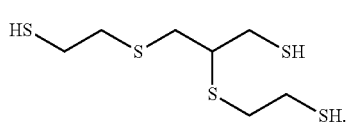

[Formula 1]

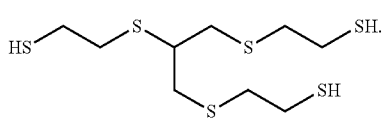

[Formula 2]

5. An optical composition comprising:
an isocyanate-based compound; and
a polythiol composition, wherein the polythiol composition comprises:
a first polythiol compound which provides a maximum peak in a high performance liquid chromatography (HPLC) analysis graph obtained at a wavelength of 230 nm; and
a second polythiol compound having a molecular weight greater than that of the first polythiol compound and represented by $C_9H_{20}S_6$,
wherein a ratio of a peak area of the second polythiol compound to a peak area of the first polythiol compound of the polythiol composition, which are measured through the HPLC analysis graph obtained at the wavelength of 230 nm, is 0.05 to 5.0%.

6. The polythiol composition according to claim 5, wherein the first polythiol compound includes a trifunctional polythiol compound, and the second polythiol compound includes a trifunctional polythiol compound having a molecular weight greater than that of the first polythiol compound.

7. The polymerizable composition according to claim 6, wherein the first polythiol compound is represented by Formula 1 below, and the second polythiol compound is represented by Formula 2:

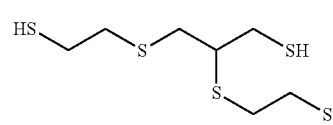

[Formula 1]

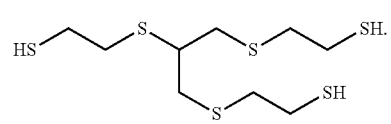

[Formula 2]

8. An optical product comprising:
A copolymer of a polythiol composition and an isocyanate-based compound,
wherein the polythiol composition comprises:
a first polythiol compound which provides a maximum peak in a high performance liquid chromatography (HPLC) analysis graph obtained at a wavelength of 230 nm; and
a second polythiol compound having a molecular weight greater than that of the first polythiol compound and represented by $C_9H_{20}S_6$,
wherein a ratio of a peak area of the second polythiol compound to a peak area of the first polythiol compound of the polythiol composition, which are measured through the HPLC analysis graph obtained at the wavelength of 230 nm, is 0.05 to 5.0%.

9. The optical product according to claim 8, a glass transition temperature of the optical product is greater than 86° C.

10. The optical product according to claim 8, a glass transition temperature of the optical product is in a range of 87 to 92° C.

* * * * *